US00PP23684P3

(12) United States Plant Patent
Wright et al.

(10) Patent No.: US PP23,684 P3
(45) Date of Patent: Jun. 25, 2013

(54) BLUEBERRY PLANT NAMED 'C95-12'

(50) Latin Name: ***Vaccinium* hybrid**
Varietal Denomination: C95-12

(75) Inventors: Gary Wright, Corindi Beach (AU); Paul Lyrene, Micanopy, FL (US)

(73) Assignees: Florida Foundation Seed Producers, Inc., Gainesville, FL (US); Costaexchange Ltd., Ravenhall (AU)

( * ) Notice: Subject to any disclaimer, the term of this patent is extended or adjusted under 35 U.S.C. 154(b) by 274 days.

(21) Appl. No.: 12/802,254

(22) Filed: Jun. 1, 2010

(65) Prior Publication Data

US 2010/0313313 P1 Dec. 9, 2010

Related U.S. Application Data

(60) Provisional application No. 61/217,857, filed on Jun. 5, 2009.

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP13,931 P2 7/2003 Lyrene

OTHER PUBLICATIONS

Pluto Upov Plant Variety Database 2011/05 retrieved on Feb. 21, 2012. Retrieved from the Internet at <http://www.upov.int/pluto/en/> 2 pp.*

* cited by examiner

*Primary Examiner* — June Hwu
(74) *Attorney, Agent, or Firm* — Davis Wright Tremaine LLP; Dale C. Hunt; Wenhua Yu

(57) ABSTRACT

A new and distinct cultivar of *Vaccinium* hybrid plant named 'C95-12', characterized by its combination of upright to bushy plant shape and strong plant growth vigor, evergreen foliage with medium to late timing of vegetative bud burst, lateness of flowering and fruiting, large berry size with oblate shape, medium to firm fruit suited to handling, attractive dark blue fruit color and small picking scar, strong berry sweetness with medium acidity. This combination results in higher quality fruit with a later availability than other varieties.

2 Drawing Sheets

Latin name of genus and species of plant claimed: *Vaccinium* hybrid.

Variety denomination: 'C95-12'.

BACKGROUND OF THE INVENTION

The present invention relates to a new and distinct perennial variety of *Vaccinium* hybrid (Southern Highbush Blueberry), which has been given the variety denomination of 'C95-12'. Its market class is that of a fruiting plant. 'C95-12' is intended for use as fresh fruit for shipping, customer pick and processing markets and as a home garden plant.

The new *Vaccinium* hybrid cultivar is a selection resulting from seedlings grown at Corindi Beach, NSW, Australia from seed extracted from fruit produced during a controlled breeding programme of *Vaccinium* at Gainesville, Fla., USA in 1993 from a cross of seed parent 'F93-29' (unpatented) and pollen parent 'F84-35' (unpatented). The new cultivar was discovered and selected as a single plant within a population of plants of *Vaccinium* hybrids in 1995 in a commercial field plantation environment at Corindi Beach, New South Wales, Australia with final selection after confirmation of traits in 1997. Selection criteria was a combination of strong plant growth vigor, lateness of ripening, good fruit flavor, large fruit size, firm fruit suited to handling, attractive dark blue fruit color and small picking scar. The selection was subsequently evaluated for a number of years at the commercial farms at Corindi Beach, New South Wales, Australia.

Asexual reproduction of the new cultivar by cutting propagation since 1995 at Corindi Beach, New South Wales, Australia and has demonstrated that the new cultivar reproduces true to type with all of the characteristics, as herein described, firmly fixed and retained through successive generations of such asexual propagation. The new variety has been primarily compared to the variety 'Southern Belle' (U.S. Plant Pat. No. 13,931). In Corindi Beach, New South Wales, Australia the plant growth habit of 'C95-12' is 'upright to bushy' whereas the plant growth habit of 'Southern Belle' is 'upright'. The plant growth vigor of 'C95-12' is 'strong to very strong' whereas the plant growth vigor of 'Southern Belle' is 'weak to medium'. The time of vegetative bud burst of 'C95-12' is usually 'medium to late' whereas the time of vegetative bud burst of 'Southern Belle' is 'late'. The fully developed leaf length of 'C95-12' is 'medium' (mean 50 mm) whereas the fully developed leaf length of 'Southern Belle' is 'medium to long' (mean 57 mm). The fully developed leaf width of 'C95-12' is 'broad' (mean 34 mm) whereas the fully developed leaf width of 'Southern Belle' is 'medium' (mean 28 mm). The fully developed leaf attitude of 'C95-12' is usually 'horizontal' whereas the fully developed leaf attitude of 'Southern Belle' is 'acute'. Corolla ridges are absent on flowers of 'C95-12' whereas corolla ridges are present on flowers of 'Southern Belle'. The time of beginning of flowering of 'C95-12' is 'late to very late' whereas the time of beginning of flowering of 'Southern Belle' is 'late'. The time of fruit ripening of 'C95-12' is 'late to very late' whereas the time of fruit ripening of 'Southern Belle' is 'late'. Berry cluster density is dense on 'C95-12' whereas berry cluster density is medium on 'Southern Belle'. The depth of the calyx basin on a berry of 'C95-12' is 'shallow' whereas the depth of the calyx basin on a berry of 'Southern Belle' is 'medium'. The diameter of the calyx basin on a berry of 'C95-12' is 'very broad' (mean 9.1 mm) whereas the diameter of the calyx basin on a berry of 'Southern Belle' is 'medium' (mean 4.9 mm). The sweetness of a berry of 'C95-12' is rated as 'strong' whereas the sweetness of a berry of 'Southern Belle' is rated as 'weak'. The acidity of a berry of 'C95-12' is rated as 'medium' whereas the sweetness of a berry of 'Southern Belle' is rated as 'weak'. This combination of fruiting attributes results in 'C95-12' being a more suitable variety for commercial and home garden use than 'Southern Belle'.

SUMMARY OF THE INVENTION

The following characteristics of the new cultivar have been repeatedly observed and can be used to distinguish 'C95-12' as a new and distinct cultivar of *Vaccinium* hybrid plant:

1. Upright to bushy plant growth habit
2. Strong plant growth vigor
3. Medium to late timing of vegetative bud burst
4. Late to very late timing of beginning of flowering
5. Late to very late timing of fruit ripening
6. Dark blue berry color
7. Berry firmness is medium to firm
8. Picking scar is dry
9. Berry diameter is large
10. Berry shape in longitudinal cross-section is oblate
11. Berry sweetness is strong
12. Berry acidity is medium Plants of the new cultivar differ from plants of the *Vaccinium* hybrid parents primarily in late to very late timing of beginning of flowering and late to very late timing of berry ripening and large berry diameter combined with strong plant growth vigor whereas the seed parent is mid season in timing of flowering and berry ripening with medium to berry diameter and the pollen parent is medium season in timing of flowering and berry ripening and medium plant growth vigor.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'C95-12'.

DETAILED BOTANICAL DESCRIPTION

Figure 1:
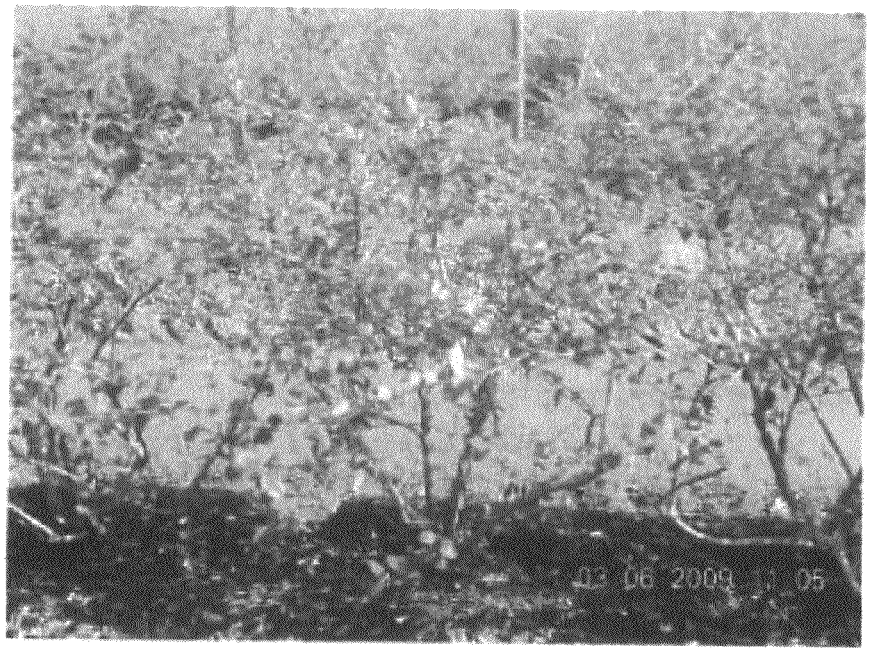
FIG. 1 illustrates a 'C95-12' plant in a commercial field planting
Figure 2:
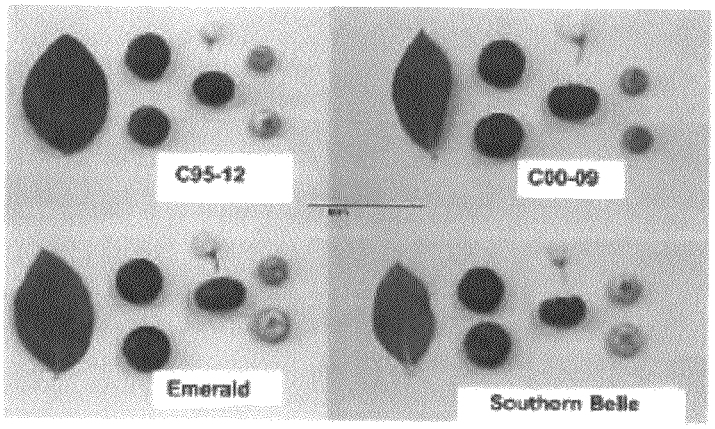
FIG. 2 illustrates a 'C95-12' leaf and berry shapes and dimensions.

The following is a detailed botanical description of a new and distinct variety of an *Vaccinium* hybrid ornamental plant known as 'C95-12'. Plant observations were made on plants grown in Corindi Beach, New South Wales, Australia. Unless indicated otherwise, the descriptions disclosed herein are based upon observations made from August to October 2007 of mature 'C95-12' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'C95-12' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on *The Royal Horticultural Society Color Chart*, of The Royal Horticultural Society, London, 2007 edition.

Botanical classification: *Vaccinium* hybrid cultivar C95-12.

Parentage:

*Parents*.—Seed parent 'F93-29' (unpatented) and pollen parent 'F 84-35' (unpatented).

Plant:

*Growth habit*.—Plants are upright to bushy. Growth vigor is strong. Plant height is 1.9 m. Plant width is 1.2 m. Flower bud density is medium. Twigginess is low. Time of beginning of leaf bud burst is medium to late (early August) when grown as an evergreen in Australia. Time of beginning of flowering is late to very late (mid September) when grown as an evergreen in Australia. Time of fruit ripening is late to very late (late October) when grown as an evergreen in Australia.

Stem:

*Suckering tendency*.—Plants typically have 5-7 major canes per plant from a base 30 cm in diameter on 6 year old plants.

*Canes*.—Erect to semi-erect with moderate branching; color greyed orange 198C; 2 year old cane diameter 12 mm, colored greyed orange 177B, some flaking of bark, current season wood diameter 3-4 mm, colored yellow green 144C. Internode length on strong, new shoots 15-20 mm.

*Fruiting wood*.—Numerous twigs to 10 cm in length.

*Surface texture of new wood*.—Smooth.

Fully developed leaf: Length medium 48-52 mm. Width broad approximately 32-36 mm. Shape elliptic. Color of upper side yellow green 137A. Intensity of color medium. Margin entire. Undulation of margin absent or very weak. Pubescence of upper side absent. Pubescence of lower side absent. Cross sectional profile flat. Longitudinal profile straight. Attitude horizontal.

*Inflorescence: Average size approximately* 50 mm long with diameter 28 mm. Length of peduncle to 12 mm. Surface texture of peduncle is smooth. Color of peduncle is yellow green RHS 144D. Length of pedicel medium 5-7 mm. Surface texture of pedicel is smooth. Color of pedicel is yellow green RHS 144C. Number of flowers per cluster median 7. Flower cluster density is medium-dense.

Flowers: Length of corolla tube short to medium(to 10 mm). Width of corolla tube narrow to medium (to 9 mm). Corolla aperture diameter 4 mm. Color of corolla white 155D. Anthocyanin coloration of corolla absent or very weak. Corolla ridges absent. Protrusion of stigma absent. Fragrance weak. Shape urceolate. Abundance of pollen high. Color of pollen white to yellow white. Calyx (with sepals) diameter 5-6 mm. Calyx color of upper side green 138A.

Productivity: 3 to 4 kg per season from 3-4 year old plants planted at 3.0 m×0.9 m density.

Cold hardiness: 'C95-12' has not been grown in all environments including harsh winter environments. Cold tolerance is expected to be low. Plants have survived winter freeze in Australia to minus 8° C. with minimal winter dieback of young shoots and resultant loss of fruit and flowers, poor growth vigor.

Chilling requirement: 'C95-12' has not been grown in all environments and is typically grown as an evergreen crop where chilling hours are not important. 'C95-12' is classed as 'low chill', typical of Southern Highbush Blueberry varieties with an estimated chilling requirement of 250 hours (not tested).

Leafing: Plants retain leaves year round (at Corindi Beach, NSW Australia) and 'C95-12' is grown commercially as an evergreen crop. New leafing occurs in mid August at Corindi Beach, NSW Australia.

Fruit: Unripe fruit color intensity medium. Unripe fruit color 144A. Cluster density is dense with range 5 to 11 berries per cluster. Diameter is large (mean 19.4 mm). Height is medium-tall (mean 15 mm). Weight medium-heavy (approximately 3.0 g). Shape oblate. Attitude of calyx erect. Diameter of calyx basin very broad (mean 9.1 mm). Depth of calyx basin is shallow (to 1.0 mm). Intensity of bloom strong. Intensity of blue color of skin with bloom removed is dark. Color of skin 202A. Color of flesh approximates to yellow green RHS145D to RHS 150D. Sweetness when ripe strong. Firmness when ripe medium to firm. Acidity when ripe medium. Size of scar is small (1.0-1.5 mm). Storage quality good.

*Date of* 50% *maturity*.—Approximately 30$^{th}$ October at Corindi Beach, NSW Australia.

*Fruit development period*.—Approximately 55 days in protected cultivation at Corindi Beach, NSW Australia.

Self-fruitfulness: C95-12 has shown a moderate degree of self-fruitfulness, and it's recommended to interplant with other highbush varieties that overlap in bloom.

Seed: Seed color greyed orange 165B. Seed abundance in fruit medium (mean 60 seeds per fruit). Seed size 1.6-1.8 mm long for fully developed seeds.

Tolerance to disease: C95-12 has shown moderate resistance to root disease (*phytophthora* spp) and good resistance to blueberry rust compared to the commercial variety 'Southern Belle'. Also demonstrates moderate to low resistance to the fruit disease Anthracnose (*Colletotrichum gleosporoides*).

What is claimed is:

1. A new and distinct cultivar of *Vaccinium* hybrid plant named 'C95-12', substantially as herein shown and described.

* * * * *